United States Patent [19]

Brand

[11] 4,083,863

[45] Apr. 11, 1978

[54] PROCESS FOR THE PREPARATION OF CYCLOPROPANE CARBOXYLIC ACIDS AND ESTERS

[75] Inventor: William Wayne Brand, Hopewell, N.J.

[73] Assignee: American Cyanamid Corporation, Stamford, Conn.

[21] Appl. No.: 691,803

[22] Filed: Jun. 1, 1976

[51] Int. Cl.$^2$ .................. C07C 120/00; C07C 121/46; C07C 69/74; C07C 69/78
[52] U.S. Cl. .......................... 260/465 D; 260/329 R; 260/464; 560/8; 560/11; 560/21; 560/51; 560/52; 560/83; 560/86; 560/124; 560/147
[58] Field of Search ............. 260/468 H, 464, 465 D, 260/470, 471 R, 475 SC; 530/124, 51, 52, 21, 11

[56] References Cited

U.S. PATENT DOCUMENTS 3,823,177  7/1974  Fanta et al. ...................... 260/468 G
3,853,952  12/1974  Kishida et al. .................. 260/465 H

OTHER PUBLICATIONS

Payne, J. Org. Chem., 32 (1967), pp. 3351-3355.

*Primary Examiner*—Joseph Paul Brust
*Attorney, Agent, or Firm*—H. G. Jackson

[57] ABSTRACT

Certain derivatives of cyclopropane carboxylic acid and their esters are useful and valuable intermediates for the preparation of broad spectrum pyrethroid type pesticides. The invention provides a novel method for the preparation of the derivatives of cyclopropane carboxylic acid and esters from stable sulfonium ylides.

13 Claims, No Drawings

PROCESS FOR THE PREPARATION OF CYCLOPROPANE CARBOXYLIC ACIDS AND ESTERS

BACKGROUND OF THE INVENTION

1. Field of the Invention

The invention pertains to the synthesis of organic chemicals which are useful pesticides.

2. Description of the Prior Art

Pyrethroid type insecticides and pesticides possess broad spectrum activity, in addition they have as a general rule low mammalian toxicity and are found to be non-persistent in the environment. Thus this class of insecticidal-pesticidal compounds is of great commercial interest and economical, high yield processes affording the pesticides are much sought after and offer considerable advantages from a manufacturing point of view.

Cyclopropane carboxylic acid and certain derivatives thereof are useful and valuable pyrethroids and intermediates for the preparation of pyrethroid type insecticides and pesticides and there are several art procedures which can be utilized to prepare the above referred to substituted cyclopropane carboxylic acid intermediates.

One potentially advantageous method of preparation of substituted cyclopropane carboxylic acids is taught by G. B. Payne, *J. Org. Chem.*, 32, 3351 (1967), wherein ethyl (dimethylsulfuranylidene)acetate (II) is reacted with activated olefinic compounds (e.g. an olefine of formula III) to yield the corresponding cyclopropane carboxylic acid ester (IVa) as hereinbelow graphically illustrated:

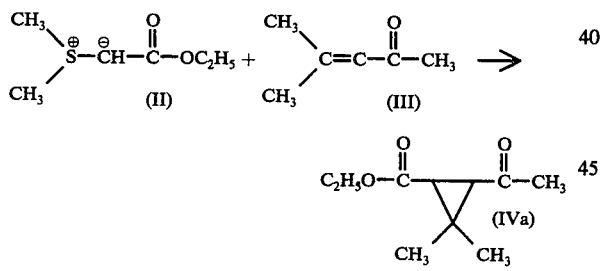

The ylide utilized in the above reaction can be conveniently prepared by reacting dimethyl sulfide with an equimolar or excess amount of ethyl bromoacetate to obtain the corresponding sulfonium salt (I) as hereinbelow illustrated:

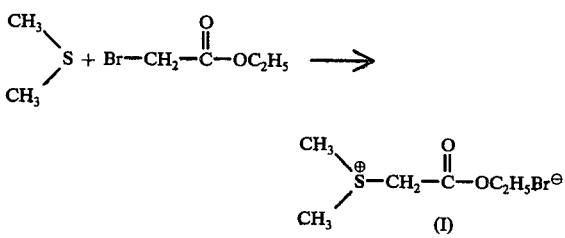

which is then converted to the above ylide (II) with a base:

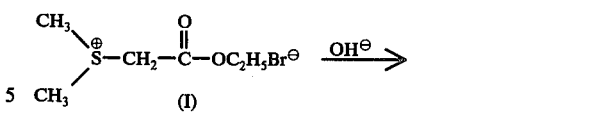

Indeed, W. I. Fanta and J. I. Schulman, U.S. Pat. No. 3,823,177 issued July 9, 1974, utilize Payne's method to prepare ethyl 2,2-dimethyl-4,5-benzospiro[2,4]hepta-4,6-diene-1-carboxylate (IVb) by reacting Payne's ylide (II) with 1-isopropylideneindene in refluxing dry methylene chloride under an argon atmosphere as hereinbelow graphically illustrated:

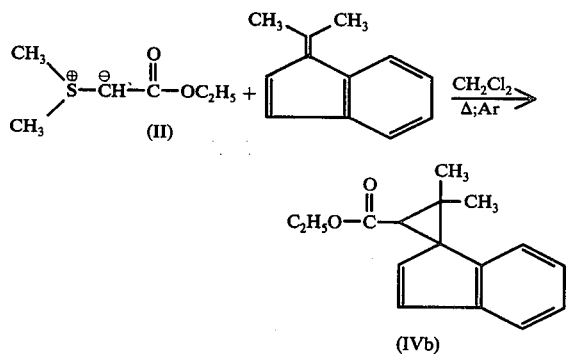

The reactions demonstrated above are useful laboratory procedures and yield the desired intermediates and products in satisfactory yields. However, because of poor thermal stability of the sulfonium salt (I) which decomposes at moderately low temperatures as illustrated below:

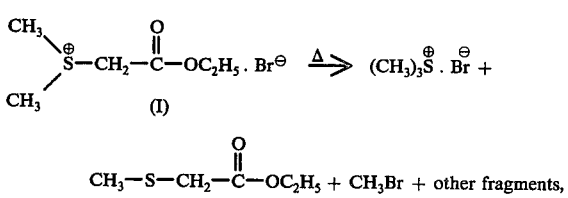

and, more particularly, because of the thermal and hydrolytic instability of the ylide (II) as illustrated below:

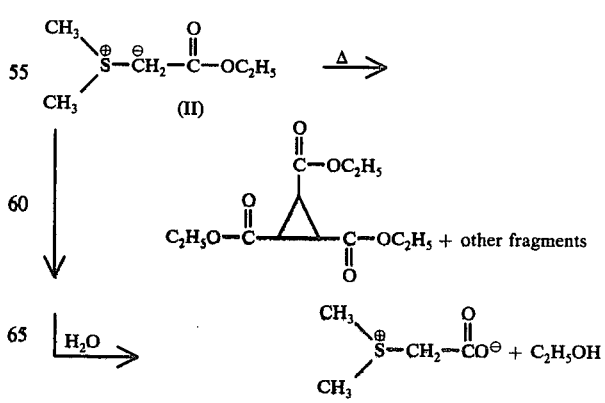

the utility of these (and similar) reagents in the preparation of cyclopropane carboxylic acids in large amounts is impractical. Since the scaling-up of reactions necessarily involves increased reaction times as well as longer separation and charging cycles, utilization of unstable intermediates necessarily means reduced product yields.

Furthermore formula (I) sulfonium salt is strongly hygroscopic, and requires therefore extra precautions in preparing, handling and storing this intermediate to avoid additional losses.

SUMMARY OF THE INVENTION

The invention is a process for the preparation of compounds of formula (IV):

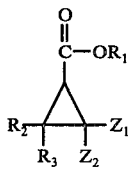
(IV)

wherein $R_1$ is alkyl $C_1-C_4$, m-phenoxybenzyl; $R_2$ and $R_3$ each are hydrogen, alkyl $C_1-C_8$, benzyl, phenyl, $C_1-C_3$ alkylphenyl or halophenyl; or $R_2$ and $R_3$ taken together represent an alkylene $C_2-C_7$ group; $Z_1$ and $Z_2$ each are $-CO_2R_4$, $-COR_5$, $-CHO$, $-CN$, $-NO_2$, $-SO_2R_6$ or one of $Z_1$ or $Z_2$ may also be $R_7$, and when $Z_1$ and $Z_2$ are taken together with the carbon atom to which they are attached they form a cyclopentadienyl or benzocyclopentadienyl group, and when one of $Z_1$ or $Z_2$ and one of $R_2$ or $R_3$ are taken together with the carbon atoms to which they are attached they form a cyclohexane-1-one-group; $R_4$, $R_5$ and $R_6$ each are alkyl $C_1-C_8$, phenyl, $C_1-C_3$ alkylphenyl or halophenyl; $R_7$ is hydrogen, alkyl $C_1-C_8$, phenyl, $C_1-C_3$ alkylphenyl or halophenyl; comprising the following steps: (a), reacting tetrahydrothiophenyl with one to 1.2 molar equivalent of a compound of the formula:

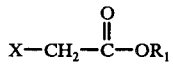

wherein $R_1$ is as hereinabove defined and X is bromine or chlorine, neat or in the presence of an inert solvent at a temperature from about 15° to 35° C. for a period of time sufficient to obtain a compound of formula (V)

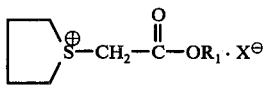
(V)

wherein $R_1$ and X are as hereinabove defined; (b), reacting the formula (V) compound with an equimolar or excess amount of an alkali metal hydroxide or carbonate in the presence of a two-phase mixture of an inert solvent and water at a temperature from about 10° to 50° C. for a period of time sufficient to obtain a compound of formula (VI):

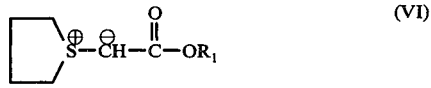
(VI)

wherein $R_1$ is as hereinabove defined; (c), reacting the formula (VI) compound with a one to 1.2 molar equivalent of a compound of formula (IX):

IX wherein $R_2$, $R_3$, $Z_1$ and $Z_2$ are as hereinabove defined, except that when one of $Z_1$ or $Z_2$ and one of $R_2$ or $R_3$ are taken together with the olefinic carbon atoms to which they are attached, then formula (IX) compound is 2-cyclohexene-1-one; in an anhydrous inert solvent or without solvent under a blanket of inert gas.

DETAILED DESCRIPTION

The novel process of the present invention yielding the desired derivatives of cyclopropane carboxylic acid utilizes 1-(carbalkoxymethyl)tetrahydrothiophenium halide esters, represented by formula (V):

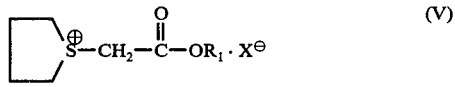
(V)

and the ylides (VI) derived therefrom:

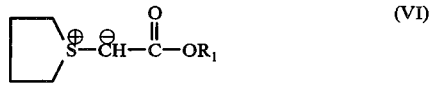
(VI)

wherein $R_1$ is selected from alkyl $C_1-C_4$, m-phenoxybenzyl and X is bromine or chlorine. Surprisingly formulae (V) and (VI) compounds are quite stable and thus offer unexpected and marked advantages for the preparation of cyclopropane carboxylic acid derivatives of the present invention.

First of all, whereas formula (I) sulfonium salts are strongly hygroscopic and absorb moisture rapidly from the air even at moderate levels of relative humidity, the analogous formula (V) tetrahydrothiophenium salts are much less hygroscopic and thus absorb moisture from the air much more slowly, and then only at much higher levels of relative humidity as hereinbelow illustrated in Table I.

Table I

| | | % Weight Gain | |
|---|---|---|---|
| % Relative Humidity | Time, Days | $(CH_3)_2\overset{\oplus}{S}-CH_2-\overset{O}{\underset{\|}{C}}-OC_2H_5 \cdot X^{\ominus}$ | $\begin{array}{c}\phantom{x}\\\overset{\oplus}{S}-CH_2-\overset{O}{\underset{\|}{C}}-OC_2H_5 \cdot X^{\ominus}\end{array}$ |
| 52 | 3 | 11 | — |
| | 5 | — | 0 |
| 76 | 3 | 18 | — |
| | 5 | — | 0 |
| 81 | 2 | — | 4 |
| | 4 | 27 | — |

Table I-continued

| | | % Weight Gain | |
|---|---|---|---|
| % Relative Humidity | Time, Days | $(CH_3)_2\overset{\oplus}{S}-CH_2-\overset{O}{\overset{\|}{C}}-OC_2H_5 \cdot X^{\ominus}$ | [tetrahydrothiophenium]$\overset{\oplus}{S}-CH_2-\overset{O}{\overset{\|}{C}}-OC_2H_5 \cdot X^{\ominus}$ |
| 5 | | — | 12 |

This improved behavior allows the ready preparation and isolation of the formula V salts on a large scale without the extraordinary precautions of maintaining the relative humidity below a certain level or of using other devices to avoid pick-up of water.

Significantly, formula (V) tetrahydrothiophenium salts also differ in their behavior from formula (I) sulfonium salts, when exposed to moderately elevated temperatures. Under these conditions they too undergo thermal decomposition, however when the thus-obtained mixture of decomposition products is cooled down, the formula (V) tetrahydrothiophenium salt re-forms, indicating that the aforesaid thermal decomposition is a reversible reaction in the case of this compound while the thermal decomposition of formula (I) sulfonium salts is irreversible.

Both formula (I) sulfonium and formula (V) tetrahydrothiophenium salts can be prepared in high yields under similar conditions, however the unexpected and not obvious reversible thermal decomposition of formula (V) tetrahydrothiophenium salts is of extreme significance in the process of the present invention.

Both formula (II) and formula (VI) ylides can be prepared with equal ease from the corresponding sulfonium (I) and tetrahydrothiophenium (V) salt. However, the tetrahydrothiophenium ylide of formula (VI) is surprisingly and unexpectedly much more stable under the same conditions of formation than is the sulfonium ylide of formula (II) as illustrated in Table II below:

Table II

| Ylide Formed | Reaction Temperature | Time | % Yield |
|---|---|---|---|
| $(CH_3)_2\overset{\oplus}{S}-\overset{\ominus}{C}H-COOC_2H_5$ | <20° C | 45 min. | 94 |
| | <20° C | 2½ hrs. | 75 |
| | <20° C | 10 min. | 100 |
| [ring]$\overset{\oplus}{S}-\overset{\ominus}{C}H-COOC_2H_5$ | 20° C-25° C | 16 hrs. | 100 |
| | 49° C-50° C | 1 hr. | 91 |

Although both formulae (II) and (VI) ylides can be used to prepare cyclopropane carboxylic acids and esters thereof, the increased stability of formula (VI) tetrahydrothiophenium ylides over that of formula (II) sulfonium ylides allows for much more latitude in reaction conditions and therefore better yields and cleaner products are obtained because fewer unwanted side reactions occur due to the thermal decomposition of the ylide. Thus the new tetrahydrothiophenium salt (V) and tetrahydrothiophenium ylide (VI) allow reaction scale-up and extended reaction cycles without yield loss.

Advantageously the novel process of the present invention consists of the following reaction steps:

Tetrahydrothiophene is reacted with an equimolar or slight excess (10 to 20%) amount of an ester of a haloacetic acid in an inert solvent, such as acetone, methyl ethyl ketone, chloroform, ethylene dichloride and the like at a temperature range from about 15° to 35° C, and preferably 20° to 25° C for a period of time from 1 to 3 days or until the reaction is complete to afford the corresponding formula (V) tetrahydrothiophenium salt as hereinbelow graphically illustrated:

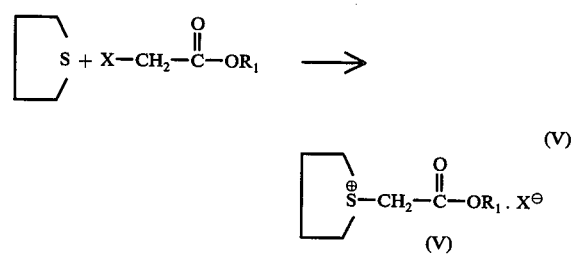

wherein $R_1$ is selected from alkyl $C_1$-$C_4$, m-phenoxybenzyl X is bromine or chlorine.

The thus obtained formula (V) tetrahydrothiophenium salt is then reacted with an equimolar or excess amount of an aqueous base selected from sodium or potassium hydroxide or carbonate or mixtures thereof in the presence of an inert solvent selected from methylene chloride, ethylene dichloride, chloroform and the like, at a temperature range about from 10° to 50° C, and preferably 15° to 25° C for a period of time from about 10 minutes to 16 hours and preferably 10 minutes to 3 hours, to afford the corresponding tetrahydrothiophenium carboxymethylide ester (VI), as hereinbelow graphically illustrated:

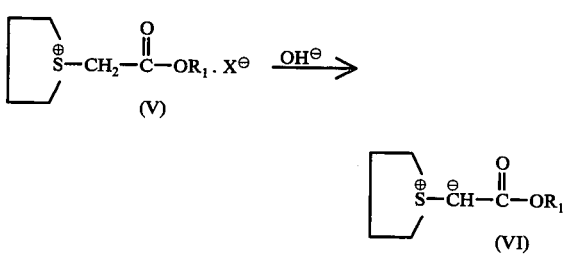

wherein $R_1$ and X are as defined above.

The tetrahydrothiophenium ylide of formula (VI) may be isolated from the reaction mixture if desired, and used neat in the next reaction step, but may also be used without isolation in the presence of the inert solvent in which it was dissolved in the previous step, under anhydrous conditions and under a blanket of inert gas such as nitrogen. The appropriate olefin, activated by substituents to promote nucleophillic addition across the double bond, is added in equimolar or slight (10 – 20%) excess amounts to the ylide (VI) or an anhydrous solution thereof, and the reaction mixture is then heated at a temperature range from about 25° to 100° C, and preferably 25° to 50° C for a period of time sufficient to obtain the maximum yield of the desired formula (IV) cyclopropane carboxylic acid ester as determined by glc. The above reaction may be graphically illustrated as follows:

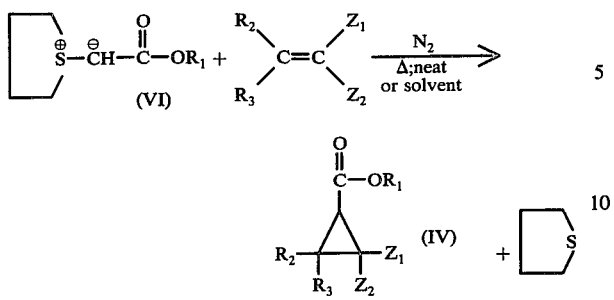

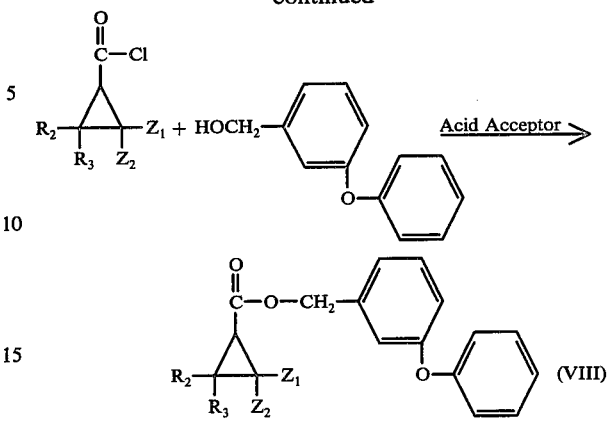

wherein in the above-illustrated reaction sequence $R_1$ is alkyl $C_1$–$C_4$ and $R_2$, $R_3$, $Z_1$ and $Z_2$ are as hereinabove defined and formula (VIII) compound is a pyrethroid type pesticide.

Obviously, when the ester group ($R_1$) of ylide (VI) is m-phenoxybenzyl then the above formula (VIII) pyrethroid type insecticide-pesticide is obtained advantageously in one step, by reacting the ylide with the appropriate olefin as hereinabove defined, without the necessity of going through the above depicted reaction scheme leading to formula (VIII) pesticide. Thus:

wherein $R_1$ is selected from alkyl $C_1$–$C_4$, m-phenoxybenzyl $R_2$ and $R_3$ are members independently selected from hydrogen, alkyl $C_1$–$C_8$, benzyl and phenyl, which may optionally be substituted with alkyl $C_1$–$C_3$ or halogen; or $R_2$ and $R_3$ taken together represent an alkylene $C_2$–$C_7$ group; $Z_1$ and $Z_2$ are members which will promote nucleophillic addition across the olefinic double bond, and are selected from —$CO_2R_4$, —$COR_5$, —CHO, —CN, —$NO_2$, —$SO_2R_6$, or one of $Z_1$ or $Z_2$ may also be $R_7$, and when $Z_1$ and $Z_2$ are taken together with the olefinic carbon atom to which they are attached they form a cyclopentadienyl or benzocyclopentadienyl group, and when one of $Z_1$ or $Z_2$ and one of $R_2$ or $R_3$ are taken together with the olefinic carbon atoms to which they are attached they form 2-cyclohexene-1-one; $R_4$, $R_5$ and $R_6$ each are selected from alkyl $C_1$–$C_8$, phenyl optionally substituted with alkyl $C_1$–$C_3$ or halogen; $R_7$ is a member selected from hydrogen, alkyl $C_1$–$C_8$, phenyl optionally substituted with alkyl $C_1$–$C_3$ or halogen.

The thus-obtained esters of cyclopropane carboxylic acid represented by formula (IV) may be used to good advantage to prepare highly active pyrethroid type pesticides therefrom by standard laboratory methods.

Conveniently a formula (IV) ester is hydrolized to the corresponding carboxylic acid with a base such as sodium or potassium hydroxide in aqueous alcohol; the carboxylic acid of formula (VII) is isolated, and converted to the acid chloride. Finally the acid chloride is reacted with the appropriate alcohol in an inert solvent in the presence of an acid acceptor to afford an above referred-to pyrethroid type pesticide. This reaction scheme may be graphically illustrated as follows:

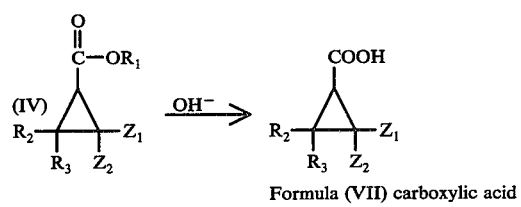

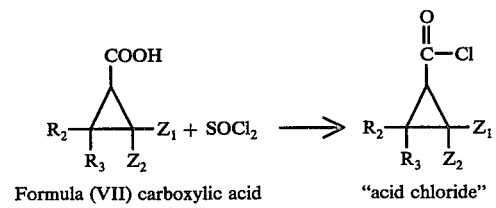

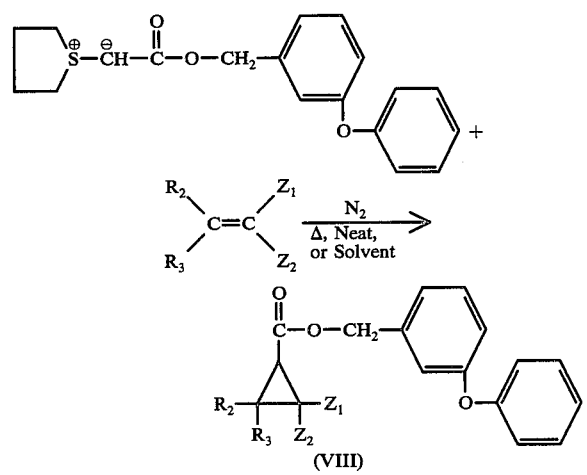

wherein $R_2$, $R_3$, $Z_1$ and $Z_2$ are as hereinabove defined.

Formula (VIII) pyrethroid type insecticides-pesticides may be formulated as emulsifiable concentrates, low volume sprays, wettable powers and the like by generally known practices and are used in amounts from .01 lbs per acre to 1.5 lbs per acre to control undesired insect pests of agriculturally important crops.

The following non-limiting examples further illustrate the present invention.

EXAMPLE 1

Preparation of 1-(Carboxymethyl)tetrahydrothiopheium bromide, ethyl ester

A mixture of tetrahydrothiophene (72 ml, 0.81 mole) ethyl bromoacetate (86 ml, 0.81 mole) and acetone (240 ml) is stirred at room temperature. After about 5 minutes, the clear solution becomes cloudy. Stirring is continued for 3 days, after which the white crystalline solid is collected by filtration, washed with acetone and air dried to give 182.4 g (88% yield) of product, m.p. 126.5° to 130° C. [lit. m.p. 122° C to 124° C, G. Schmidt and J. Gosselck, *Tetrahedron Letters,* 344 (1969)].

By the above procedure, but substituting m-phenoxybenzyl bromoacetate for ethyl bromoacetate, 1-(carboxymethyl)tetrahydrothiophenium bromide-, m-phenoxybenzyl ester is obtained.

EXAMPLE 2

Reversible thermal decomposition of 1-(Carboxymethyl)tetrahydrothiophenium bromide, ethyl ester When a suspension of 1-(carboxymethyl)tetrahydrothiophenium bromide, ethyl ester (1.0 g) in acetone (10 ml) is heated at reflux for 1 hour, the mixture becomes homogeneous. Cooling gives a very small amount of solids. Concentration of the reaction mixture yields a residue, which is shown by infrared to contain ethyl bromoacetate and very little starting material.

If the residue is allowed to stand at room temperature for 2 days, it slowly solidifies to a white solid (0.5 g), shown by infrared to be 1-(carboxymethyl)tetrahydrothiophenium bromide, ethyl ester containing no ethyl bromoacetate.

EXAMPLE 3

Preparation of 1-(carboxymethyl)tetrahydrothiophenium chloride, tert-butyl ester When a mixture of tert - butyl chloroacetate and tetrahydrothiophene are allowed to stand at room temperature for several days, a white crystalline solid is deposited. Filtration and drying yields the title product, m.p. 148° to 150° C.

EXAMPLE 4

Preparation of Tetrahydrothiophenium carboxymethylide, ethyl ester

A suspension of ethyl 1-(carboxymethyl)tetrahydrothiophenium bromide (10.2 g, 0.04 mole) in ethylene dichloride (30 ml) is stirred and cooled in an ice bath to 5° C. To this mixture is added over about 1 minute a mixture of 50% aqueous sodium hydroxide (3.52 g, 0.044 mole) and saturated potassium carbonate (24 ml) solution. The temperature of the reaction mixture rises to 15° C during the addition. After 15 minutes of stirring, the bath is removed, and stirring continued for an additional 30 minutes. The two phase reaction mixture is filtered to remove suspended solids, and the phases are separated. The ethylene dichloride solution is dried and used as is in the subsequent reaction.

If the solvent is removed, the ylide is recovered in a quantitative yield.

In an analogous experiment, using chloroform as the solvent, concentration of the dried organic phase also gives a quantitative yield of ylide whose infrared shows a strong band at 1600–1620 cm$^{-1}$, and very little at 1720 cm$^{-1}$, indicating high quality ylide. NMR shows two regions for the α-protons on the tetrahydrothiophene ring, presumably due to being syn and anti to the carbethoxymethine group. The spectra are entirely consistent with the assigned structure.

By the above procedure, but substituting 1-(carboxymethyl)-tetrahydrothiophenium bromide-, m-phenoxybenzyl ester, tetrahydrothiophenium carboxymethylide, -m-phenoxylbenzyl ester is obtained.

EXAMPLE 5

Example 4 is repeated, except with saturated potassium carbonate solution as the only base present. The ylide is obtained in quantitative yield.

EXAMPLE 6

Preparation of Dimethyl-carboxymethylsulfonium bromide, ethyl ester

To a solution of ethyl bromoacetate (1836 g, 11.0 mole) in acetone (3500 ml) containing seed crystals of the title compound, dimethyl sulfide (850 g, 13.75 mole, 25% excess) is added over about 20 minutes. The flask is cooled in a water bath. After about 80% of the dimethyl sulfide is added, product begins to precipitate from the solution. After 3 days the white solid is collected by filtration and washed with 1000 ml of acetone. The product is then air dried to yield 82% (2055 g) of white crystals, m.p. 79.5° to 81.5° C (dec). 1R shows a carbonyl stretch at 1730 cm$^{-1}$.

If this reaction is run at elevated temperature, the only solid isolated is trimethylsulfonium bromide.

EXAMPLE 7

Preparation of 3,3-Dimethylspiro[cyclopropane-1,1'-indene]-2-carboxylic acid, ethyl ester A mixture of a solution of the "ylide" prepared by the method of Example 4 (0.04 mole) and distilled isopropylideneindene (6.65 g, 94% pure, 0.04 mole) is stirred in a nitrogen atmosphere while being heated at 50° C in a bath.

The course of the reaction is followed by gas chromatography [Instrument: HP 7610A; Column: 43 inches by 6 mm OD; packing: 3% SP2250/3.95% SP2401 on 100/120 Gas-Chrom Q; programmed: post injection 125° C/4 min; level 1—, 145° C at 15° C/min., hold 30 min.]. Aliquots are periodically removed from the reaction mixture and diluted about 1:5 with chloroform. 1-Isopropylideneindene has a retention time of about 4 minutes, the product appears as two partially resolved (syn and anti) peaks with a retention time of about 10 minutes. Several small extraneous peaks are also present, but do not appear to change significantly during the course of the reaction. The % conversion is calculated by measuring the area of the peak due to each material and applying the following equation:

$$\% \text{ Conversion} = \frac{\text{Area of product}}{\text{Area of benzofulvene} + \text{Area of product}} \times 100$$

After 24 hours the reaction is 90% complete.

The product is readily separated from 1-isopropylideneindene on a silica gel dry column using 1:3 ethylene dichloride:hexane. Analysis calculated for $C_{16}H_{18}O_2$: C, 79.31; H, 7.49. Found: C, 79.20; H, 7.60.

By the above procedure, but substituting tetrahydrothiophenium carboxymethylide-, m-phenoxybenzyl ester and tetrahydrothiophenium carboxymethylide-, 3,3-dimethylspiro[cyclopropane-1,1'-indene]-2-carboxylic acid, m-phenoxybenzyl ester and 3,3-dimethylspiro[cyclopropane-1,1'-indene]-2-carboxylic acid, are obtained, respectively.

EXAMPLE 8

Example 7 is repeated, except that the reaction is held at 80° to 90° C. In about 2 hours a 66% conversion is achieved and no further reaction takes place.

EXAMPLE 9

The procedure of Example 8 is repeated except that dimethylsulfonium carboxymethylide ethyl ester is reacted with 1-isopropylideneindene. A 54% conversion of 1-isopropylideneindene to the corresponding cyclopropane carboxylic acid ethyl ester is achieved after 18 hours at 80° to 90° C.

EXAMPLE 10

Example 8 is repeated but with methylene chloride (at reflux: 45° C) as reaction solvent. An 86% conversion is obtained in 117 hours.

EXAMPLE 11

Repeating the procedure of Example 10 but substituting benzene for methylene chloride (at 86° C) gives a 69% conversion after 88 hours.

EXAMPLE 12

Preparation of Spiro[2,4-]hepta-4,6-diene-1-carboxylic acid, 2,2-dimethyl-, ethyl ester A solution of tetrahydrothiophenium carboxymethylide ethyl ester (2650 g, 15.2 moles) in methylene chloride (4000 ml total volume) is added slowly to a solution of 6,6-dimethylfulvene (15.2 moles) in methylene chloride (about 2000 ml total volume) at 15° C. The addition is carried out at such a rate that the temperature never exceeds 35° to 40° C. After stirring about 90 minutes at ambient temperature, the reaction is checked by glc, which shows a greater than 95% conversion to the cyclopropane carboxylic acid ester.

By the above procedure, but substituting tetrahydrothiophenium carboxymethylide m-phenoxybenzyl ester, spiro[2,4]hepta-4,6-diene-1-carboxylic acid, 2,2-dimethyl m-phenoxybenzyl ester is obtained.

EXAMPLE 13

Preparation of Dimethylsulfonium carboxymethylide, ethyl ester

To a stirred mixture of dimethylcarboxymethylsulfonium bromide, ethyl ester (1791 g, 7.82 mole) and ethylene dichloride (6000 ml) a mixture of saturated aqueous potassium carbonate (16.34 lbs) and 50% aqueous sodium hydroxide (1.52 lbs) is added at 10° to 16° C in about ½ hour. The reaction mixture is stirred an additional ½ hour, the phases are split and the ethylene dichloride solution dried 1 hour over anhydrous potassium carbonate. The title compound is obtained in 56% yield by evaporation of the solvent.

EXAMPLE 14

Preparation of Tetrahydrothiophenium carboxymethylide, ethyl ester

To a rapidly stirred mixture of 1-(carboxymethyl)-tetrahydrothiophenium bromide ethyl ester (1786 g, 7.0 mole) and ethylene dichloride (7143 g, 5500 ml) a mixture of saturated potassium carbonate solution (7396 g) and 50% aq. sodium hydroxide (616 g, 7.7 mole) is added at 10° to 16° C in about ½ hour. The reaction mixture is stirred an additional ½ hour, filtered and the two phases separated. The ethylene dichloride solution is dried an hour over 350 g anhydrous $Na_2SO_4$, filtered and stored overnight. The ethylene dichloride is removed under vacuum to yield 1157 g of a yellow liquid, 96% pure by NMR analysis. Thus 1110 g of ylide is obtained (yield: 91% of theory).

EXAMPLE 15

Preparation of 2,2-Dimethyl-4,5-benzospiro[2,4]hepta-4,6-diene-1-carboxylic acid, m-phenoxybenzyl ester

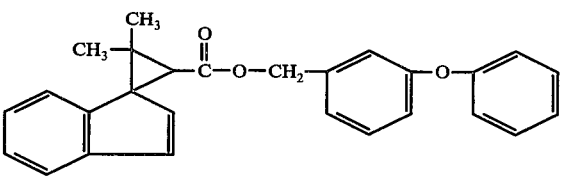

To 4.3 g (0.02 mol) of 2,2-dimethyl-4,5-benzospiro-2,4-hepta-4,6-diene-1-carboxylic acid in either hexane/benzene or benzene is added 8 ml of thionyl chloride. The solution is then stirred for 12 hours at room temperature. The solvent is then removed in vacuo leaving 4.7 g of an orange liquid (theoretical yield). Infrared indicates an acid chloride carbonyl at 1790 $cm^{-1}$.

The acid chloride and 4.0 g (0.02 mol) of m-phenoxy benzyl alcohol are dissolved in 20 ml of ether, and 2.1 g (0.02 mol) of triethylamine dissolved in 8 ml of ether is added dropwise at 20° C. Solids precipitate from solution immediately. The resulting mixture is stirred for 12 hours at room temperature. The crude product is partitioned in an ether/water mixture, and the ether layer is dried over magnesium sulfate and concentrated in vacuo to yield 7.7 g (96% theory) of a brown liquid.

The crude product is purified by dry-column chromatography on silica gel using 25% methylene chloride in hexane as a solvent. 4.4 Grams of a pale yellow liquid is obtained. The infrared spectrum shows an ester carbonyl band at 1720 $cm^{-1}$. The nuclear magnetic resonance spectrum ($CCl_4$) shows the following: δ = 1.41, 1.45, 1.58, 1.66 (4S, 6H, methyls), 2.61 (S, 1H, cyclopropane H), 4.85–5.10 (m, 2H, O—$CH_2$), 6.12 (d, 0.5H, J = 5.5 Hz, vinyl), 6.66–7.76 (m, 14.5H aromatic and vinyl).

Analyses: Calculated for $C_{27}H_{24}O_3$: C, 81.83; H, 6.06. Found: C, 82.14; H, 6.29.

EXAMPLE 16

Preparation of various cyclopropane carboxylic acid esters by the novel process of the present invention By the procedures of Examples 7, 12 or 15, the following cyclopropane carboxylic acid esters can be prepared from the corresponding olefins, as listed in Table III below.

Table III

| Olefin | Cyclopropane Carboxylic Acid Ester |
|---|---|
| (CH$_3$)$_2$C=CH—NO$_2$ | 2,2-dimethyl-3-nitrocyclopropanecarboxylic acid 3-phenoxybenzyl ester |
| 2-cyclohexen-1-one | bicyclic ketone cyclopropanecarboxylic acid 3-phenoxybenzyl ester |
| (CH$_3$)$_2$C=C(CN)$_2$ | 2,2-dimethyl-3,3-dicyanocyclopropanecarboxylic acid 3-phenoxybenzyl ester |
| CH$_3$—CO—CH=C(CH$_3$)$_2$ | 2,2-dimethyl-3-acetylcyclopropanecarboxylic acid ethyl ester |
| cyclopentylidene-isopropylidene | spiro cyclopentane dimethylcyclopropanecarboxylic acid ethyl ester |
| (CH$_3$)$_2$C=CH—CHO | 2,2-dimethyl-3-formylcyclopropanecarboxylic acid 3-phenoxybenzyl ester |
| (CH$_3$)$_2$C=CH—CHO | 2,2-dimethyl-3-formylcyclopropanecarboxylic acid ethyl ester |
| 4-Cl-C$_6$H$_4$-CH=CH-CO-O-C$_6$H$_4$-4-Cl | 1-(4-chlorophenyl)-2-(4-chlorophenoxycarbonyl)cyclopropane-3-carboxylic acid 3-phenoxybenzyl ester |

Table III-continued

| Olefin | Cyclopropane Carboxylic Acid Ester |
|---|---|
| (structure) | (structure) |

EXAMPLE 17

Insecticidal Activity

The high degree of effectiveness of formula IV compounds for controlling insects is demonstrated in the following tests, wherein Tobacco budworm, *Heliothis virescens* (Fabricius); Cotton Boll Weevil, *Anthonomus grandis* (Boheman); Western Potato Leafhopper, *Empoasca abrupta* (Say) and Bean Aphid, *Aphis fabae* (Scopoli), are employed as test insect species. Procedures employed are as follows: Tobacco Budworm, *Heliothis virescens* (Fabricius).

A cotton plant with two true leaves expanded is dipped for 3 seconds with agitation in a test solution (35% water/65% acetone) containing 300, 100 or 10 ppm of test compound. A ½ to ¾-inch square of cheesecloth with about 50 to 100 budworm eggs 0–24 hours old is also dipped in the test solution and placed on a leaf of the cotton plant, all being placed in the hood to dry. The leaf with the treated budworm eggs is removed from the plant and placed in an 8-ounce Dixie cup with a wet 2 inch piece of dental wick and covered with a lid. The other leaf is placed in a similar cup with a wick and a piece of cheesecloth infested with 50–100 newly hatched larvae is added before covering the cup with a lid. After 3 days at 80° F, 50% r.h., observations of egg hatch are made, as well as kill of newly hatched larvae. Data obtained are reported as percent kill in the table below. Cotton Boll Weevil, *Anthonomus grandis* (Boheman).

A cotton plant with cotyledons expanded is dipped for 3 seconds, with agitation, in a 35% water/65% acetone solution containing 1000 ppm of test compound. The dipped plants are then placed in a hood to dry. One cotyledon is removed from the plant and placed in a 4-inch petri dish containing a moist filter paper on the bottom and 10 adult bol weevils. After 2 days at 80° F, and 50% r.h., mortality counts are made. Data obtained are reported below. Western Potato Leafhopper, *Empoasca abrupta* (Say).

A Sieve lima bean plant with the primary leaf expanded to 3 to 4 inches is dipped into a 35% water/65% acetone solution containing 100 ppm of test compound. The dipped plant is placed in the hood to dry and then a 1-inch piece of the tip of one leaf is cut off and placed in a 4-inch petri dish with a moist filter paper in the bottom. From 3 to 10 second-instar nymphs are placed in the dish and the dish is then covered. Mortality counts are made holding the thus-prepared dishes for 2 days at 80° F and 50% r.h. Bean Aphid, *Aphis fabae* (Scopoli).

Two-inch fiber pots, each containing a nasturtium plant 2 inches high and infested with 100 to 150 aphids 2 days earlier are placed on a 4 rpm turntable and sprayed with a 35% water/65% acetone solution containing 100 ppm of test compound for 2 revolutions using a DeVilbiss Atomizer and 20 psi air pressure. The spray tip is held about 6 inches from the plants and the spray directed so as to give complete coverage of the aphids and the plants. The sprayed plants are laid on their sides on white enamel trays. Mortality estimates are made after 1 day at 70° F, 50% r.h.

In these tests, permethrin and phenothrin, known pyrethroid insecticides, are used as checks for the purpose of evaluation. Data are reported in Table III as percent mortality determined at the rate indicated. From the data it can be seen that the test compounds are substantially more effective than permethrin and phenothrin against the above-named insects.

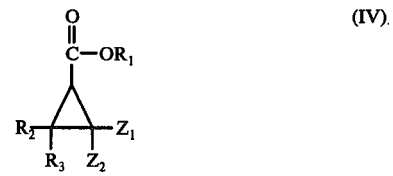

wherein $R_1$ is alkyl $C_1$-$C_4$, m-phenoxybenzyl; $R_2$ and $R_3$ each are hydrogen, alkyl $C_1$-$C_8$, benzyl, phenyl, $C_1$-$C_3$ alkylphenyl or halophenyl; or $R_2$ and $R_3$ taken together represent an alkylene $C_2$-$C_7$ group; $Z_1$ and $Z_2$ each are —$CO_2R_4$, —$COR_5$— —CHO, —CN, —$NO_2$, —$SO_2R_6$ or one of $Z_1$ or $Z_2$ may also be $R_7$, and when $Z_1$ and $Z_2$ are taken together with the carbon atom to which they are attached they form a cyclopentadienyl or benzocyclopentadienyl group, and when one of $Z_1$ or $Z_2$ and one or $R_2$ or $R_3$ are taken together with the carbon atoms to which they are attached they form a cyclohexane-1-one group; $R_4$, $R_5$ and $R_6$ each are alkyl $C_1$-$C_8$, phenyl, $C_1$-$C_3$ alkylphenyl or halophenyl; $R_7$ is hydrogen, alkyl $C_1$-$C_8$, phenyl, $C_1$-$C_3$ alkylphenyl or halophenyl; comprising the following steps:

a. reacting tetrahydrothiophene with a one to 1.2 molar equivalent of a compound of the formula:

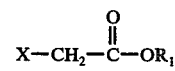

wherein $R_1$ is as hereinabove defined and X is bromine or chlorine, heat or in the presence of an inert solvent at a temperature from about 15° to 35° C. for a period of time sufficient to obtain a compound of formula (V)

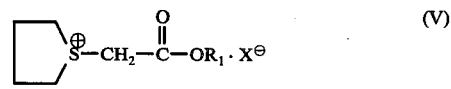

wherein $R_1$ and X are as hereinabove defined;

Table III

| Compound | Tobacco Budworm | | Boll Weevil ppm 1000, 100 | Leaf Hopper ppm 100, 10 | Aphids ppm 100, 10, 1, .1 |
|---|---|---|---|---|---|
| | Eggs ppm 300, 100, 10 | Larvae ppm 300, 100, 10 | | | |
| Cl₂C=CH—⟨⟩—CO—O—CH₂—⟨⟩—O—⟨⟩ CH₃ CH₃ Permethrin | 100, 100, 0 | 100, 100, 50 (RF) | 0, 0 (RF) (RF) 100 70 100 80 100 60 | 100, 0 | 100, 100, 100, 0 |
| CH₃ CH₃—⟨⟩—CO—O—CH₂—⟨⟩—O—⟨⟩ | 100, 100, 0 | 100, 100, 100 | 100, 0 (RF) | 100, 100 | 100, 100, 100, 0 |
| CH₃ CN CH₃—⟨⟩—CO—O—CH—⟨⟩—O—⟨⟩ | 100, 100, 0 | 100, 100, 100 | 100, 0 (RF) | 100, 100 | 100, 100, 100, 100 |
| (CH₃)₂C=CH—⟨⟩—CO—O—CH₂—⟨⟩—O—⟨⟩ CH₃ CH₃ Phenothrin | 100, 100 0 | 100, 100, 0 | 0 (RF) | 80, 0 | 100, 60 100, 100, 100, 0 |

RF = Reduced Feeding

I claim:
1. A process for the preparation of compounds of formula (IV):

b. reacting the formula (V) compound with an equimolar or excess amount of an alkali metal hydroxide or carbonate or mixtures thereof in the presence of a two-phase mixture of an inert solvent and water at a temperature from about 10° to 50° C. for a period of time sufficient to obtain a compound of formula (VI):

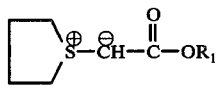 (VI)

wherein $R_1$ is as hereinabove defined;

c. reacting the formula (VI) compound with a one to 1.2 molar equivalent of a compound of formula (IX):

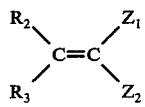 IX wherein $R_2$, $R_3$, $Z_1$ and $Z_2$ are as hereinabove defined, except that when one of $Z_1$ or $Z_2$ and one of $R_2$ or $R_3$ are taken together with the olefinic carbon atoms to which they are attached, then formula (IX) compound is 2-cyclohexene-1-one; in an anhydrous inert solvent or without solvent under a blanket of inert gas.

2. The process according to claim 1, wherein in step (a) the temperature range is 20° to 25° C. and the reaction time 1 to 3 days; in Step (b) the temperature range is 15° to 25° C. and the reaction time 10 minutes to 3 hours; in Step (c) the temperature range is 25° to 50° C. and the reaction time 3 hours to 18 hours; and the reaction is run without solvent, or the inert solvents are acetone, methyl ethyl ketone, methylene chloride, chloroform, or ethylene dichloride.

3. The process according to claim 2, wherein $R_1$ is methyl, ethyl, m-phenoxybenzyl; the compound of formula (IV) is 6,6-dimethyfulvene, 1-isopropylideneindene or 2-cyclohexene-1-one; and X is bromine or chlorine.

4. The process according to claim 2, wherein $R_1$ is methyl or ethyl; $R_2$ and $R_3$ each are methyl; $Z_1$ and $Z_2$ taken together with the carbon atoms to which they are attached form a cyclopentadieneyl group; and X is bromine or chlorine.

5. The process according to claim 2, wherein $R_1$ is methyl or ethyl, $R_2$ and $R_3$ each are methyl; $Z_1$ and $Z_2$ taken together with the carbon atom to which they are attached form a benzo[1,2]cyclopentadienyl group; and X is bromine or chlorine.

6. The process according to claim 2, wherein $R_1$ is m-phenoxybenzyl; $R_2$ and $R_3$ each are methyl; $Z_1$ and $Z_2$ taken together with the carbon atom to which they are attached form a cyclopentadienyl group; and X is bromine or chlorine.

7. The process according to claim 2, wherein $R_1$ is m-phenoxybenzyl; $R_2$ and $R_3$ each are methyl; $Z_1$ and $Z_2$ taken together with the carbon atom to which they are attached form a benzocyclopentadienyl group; and X is bromine or chlorine.

8. The process according to claim 2, wherein $R_1$ is m-phenoxybenzyl; $R_2$ is methyl; $R_3$ is benzyl; $Z_1$ and $Z_2$ are each cyano; and X is bromine or chlorine.

9. The process according to claim 2, wherein $R_1$ is m-phenoxybenzyl; $R_2$ is hydrogen; $R_3$ is phenyl; $Z_1$ is hydrogen; $Z_2$ is nitro; and X is bromine or chlorine.

10. The process according to claim 2, wherein $R_1$ is m-phenoxybenzyl; $R_2$ and $R_3$ are each methyl; $Z_1$ is hydrogen, $Z_2$ is nitro; and X is bromine or chlorine.

11. The process according to claim 2, wherein $R_1$ is m-phenoxybenzyl; $R_2$ and $R_3$ each are methyl; $Z_1$ and $Z_2$ each are cyano; and X is bromine or chlorine.

12. The process according to claim 2, wherein $R_1$ is ethyl; $R_2$ and $R_3$ each are methyl; $Z_1$ is hydrogen, $Z_2$ is

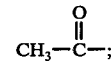

and X is bromine or chlorine.

13. The process according to claim 2, wherein $R_1$ is m-phenoxybenzyl; the compound of formula (IV) is 2-cyclohexene-1-one; and X is bromine or chlorine.

* * * * *